(12) United States Patent
Sakai et al.

(10) Patent No.: US 7,002,033 B1
(45) Date of Patent: Feb. 21, 2006

(54) CHEMICAL VAPOR DEPOSITION MATERIAL AND CHEMICAL VAPOR DEPOSITION

(75) Inventors: Tatsuya Sakai, Chuo-ku (JP); Sachiko Hashimoto, Chuo-ku (JP); Yasuo Matsuki, Chuo-ku (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 11/187,982

(22) Filed: Jul. 25, 2005

(30) Foreign Application Priority Data

Jul. 27, 2004 (JP) .............................. 2004-218311

(51) Int. Cl.
*C07F 15/00* (2006.01)
*C23C 16/00* (2006.01)

(52) U.S. Cl. .................. 556/137; 427/250; 427/255.19
(58) Field of Classification Search ................. 556/137; 427/250, 255.19
See application file for complete search history.

(56) References Cited

U.S. PATENT DOCUMENTS

| | | | | |
|---|---|---|---|---|
| 6,063,705 | A | 5/2000 | Vaartstra | 438/681 |
| 6,207,232 | B1 | 3/2001 | Kadokura | 427/252 |
| 6,420,582 | B1 | 7/2002 | Okamoto | 556/136 |
| 6,440,495 | B1 | 8/2002 | Wade et al. | 427/250 |
| 6,828,218 | B1 | 12/2004 | Kim et al. | 438/478 |
| 2002/0055001 | A1 | 5/2002 | Funakubo et al. | 428/457 |

FOREIGN PATENT DOCUMENTS

| | | |
|---|---|---|
| JP | 6-283438 | 10/1994 |
| JP | 11-35589 | 2/1999 |
| JP | 11-340435 | 12/1999 |
| JP | 2002-69639 | 3/2002 |
| JP | 2002-114795 | 4/2002 |
| JP | 2002-161367 | 6/2002 |
| JP | 2002-212112 | 7/2002 |
| JP | 2002-523634 | 7/2002 |
| JP | 2002-367992 | 12/2002 |

OTHER PUBLICATIONS

"Research Result (2) * 0.1 to 0.07 um Introduction of a new material into a gate", Nikkei Microdevices, Feb. 2000, pp. 93-106, with partial English translation.
"Electronic Parts and Materials", Nov. 2003, pp. 47-49, with partial English translation.
Tsuyoshi Kawagoe, et al., "Novel Storage-Node Contacts with Stacked Point-Cusp Magnetron Sp- TiN Barrier for Metal-Insulator-Metal $Ru/Ta_2O_5/Ru$ Capacitors in Gigabit Dynamic Random Access Memories", Japanese Journal of Applied Physics, vol. 43, No. 6A, 2004, pp. 3315-3319.
Booyong S. Lim, et al., "Atomic layer deposition of transition metals", nature materials, vol. 2, Nov. 2003, pp. 749-754.
Zhengwen Li, et al., "Synthesis and Characterization of Copper(I) Amidinates as Precursors for Atomic Layer Deposition (ALD) of Copper Metal", Inorganic Chemistry, vol. 44, No. 6, 2005, pp. 1728-1735.

*Primary Examiner*—Porfirio Nazario-Gonzalez
(74) *Attorney, Agent, or Firm*—Oblon, Spivak, McClelland, Maier & Neustadt, P.C.

(57) ABSTRACT

A chemical vapor deposition material comprising a ruthenium compound having a ligand represented by the following formula:

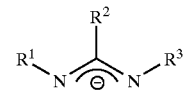

wherein $R^1$, $R^2$ and $R^3$ are each independently a hydrogen atom, fluorine atom, trifluoromethyl group or hydrocarbon group having 1 to 10 carbon atoms,
and a method of forming a ruthenium film from the chemical vapor deposition material by chemical vapor deposition.

A high-quality ruthenium film even when it is very thin can be obtained.

2 Claims, No Drawings

CHEMICAL VAPOR DEPOSITION MATERIAL AND CHEMICAL VAPOR DEPOSITION

FIELD OF THE INVENTION

The present invention relates to a chemical vapor deposition material and chemical vapor deposition.

DESCRIPTION OF THE PRIOR ART

It is becoming difficult to ensure the capacity of a memory cell with the prior art to meet drastic demand for higher integration and a finer pattern rule for semiconductor devices typified by DRAM (Dynamic Random Access Memory). To cope with this, the alteration of the materials of metal films and metal oxide films constituting these devices is becoming necessary to obtain a finer pattern rule.

Particularly, the improvement of a conductive metal film for use in the multi-layer wiring of a semiconductor device is desired. Although aluminum has been used as a wiring material, it is being replaced by copper having a resistivity 60% lower than that of aluminum. In order to improve the conductivity of this copper wiring, a low-dielectric material (Low-k material) is used as an interlayer dielectric material for this multi-layer wiring. However, an oxygen atom contained in this Low-k material is taken into the copper wiring easily to reduce its conductivity. Therefore, studies are being made on technology for forming a barrier film between the Low-k material and the copper wiring in order to prevent the movement of oxygen from the Low-k material. As the material of this barrier film, studies are being made on use of platinum and ruthenium as an insulator, all of which hardly take in oxygen from the dielectric layer and use of ruthenium oxide which has conductivity. It is known that, out of these, a platinum film is hardly processed by dry etching whereas a metal ruthenium film or ruthenium oxide film can be relatively easily processed by dry etching and can be suitably used as a barrier film material.

As dielectric materials for capacitor insulators for which a laminated film (ON film) consisting of silicon oxide and silicon nitride layers has been used, materials having a perovskite crystal structure and an extremely large dielectric constant than the ON film, such as barium titanate, strontium titanate and PZT, have been studied to achieve higher integration and a finer pattern rule. However, even when these high-dielectric materials are used as a capacitor insulator, a low dielectric layer may be formed at the interface between an electrode and a dielectric, thereby forming an obstacle to the improvement of capacitance. It is considered that this low-dielectric layer is formed by the movement of an oxygen atom from the dielectric layer to the electrode material. Then, platinum, ruthenium and ruthenium oxide are studied as electrode materials which hardly take in oxygen from the dielectric layer. It is known that a metal ruthenium film or ruthenium oxide film can be suitably used as an electrode for a capacitor having a perovskite structure dielectric as an insulator because it can be easily processed as described above (Nikkei Micro-device, pp. 93–106, February 2000, Electronic Materials, pp. 47–49, November 2003, Jpn. J. Appl. Phys., Vol. 43, No. 6A, pp. 3315–3319, 2004).

Although sputtering has been employed for the formation of the above metal ruthenium film, chemical vapor deposition is now under study to obtain a fine structure, reduce the film thickness and realize mass-production (JP-A 11-340435, JP-A 2002-161367, JP-A 2002-212112, JP-A 2002-523634 and JP-A 2002-69639) (the term "JP-A" as used herein means an "unexamined published Japanese patent application").

However, in general, a metal film formed by chemical vapor deposition has poor surface morphology as the assembly state of the fine crystals of the film is sparse. When this metal film is used as a capacitor electrode, an increase in leak current caused by the concentration of a field occurs. When a very thin electrode is to be formed so as to realize a fine pattern rule, a film having a defect that metal portions are scattered like islands and not a uniform film is obtained with the result of reduced electric conductivity. When this film is used as a capacitor electrode, a large capacitor area cannot be obtained and capacitance required for the operation of the capacitor cannot be ensured.

In order to solve the above morphology problem, studies are being made on use of bis(dipivaloylmethanato)ruthenium or ruthenocene•bis(alkylcyclopentadienyl)ruthenium as a chemical vapor deposition material (refer to JP-A 06-283438, JP-A 11-35589 and JP-A 2002-114795).

However, in the method making use of these chemical vapor deposition materials, morphology and the step coverage of a 3-D substrate are improved but the obtained film is inferior to a ruthenium film formed by sputtering in conductivity and the formed ruthenium film contains impurities in large quantities. Therefore, when a ruthenium film formed from any one of these raw materials by chemical vapor deposition is used as an electrode for DRAM, the performance of the DRAM becomes unsatisfactory.

Further, technology making use of these chemical vapor deposition materials has a problem that it is difficult to form a super thin film required for the reduction of the pattern rule (particularly, 10 nm or less) and therefore cannot realize a DRAM having a fine pattern. To realize the formation of a super thin film, monatomic layer deposition is studied and a technique for forming a metal cobalt metal copper film by the monatomic layer deposition is reported (refer to JP-A 2002-367992 and Nature Materials, Vol. 2, pp. 749–754, November 2003).

However, this method has a problem with production yield due to its complicated process.

SUMMARY OF THE INVENTION

It is an object of the present invention which has been made in view of the above problem to provide a chemical vapor deposition material which can provide a high-quality ruthenium film even when it is very thin and a simple method of forming a ruthenium film from the chemical vapor deposition material.

According to the present invention, firstly, the above object can be attained by a chemical vapor deposition material represented by the following formula (1):

wherein L is a ligand represented by the following formula (2):

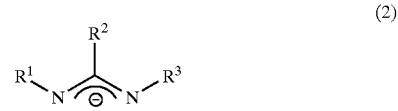

wherein $R^1$, $R^2$ and $R^3$ are each independently a hydrogen atom, fluorine atom, trifluoromethyl group or hydrocarbon group having 1 to 10 carbon atoms, X is a hydrogen anion, halogen anion, monovalent hydrocarbon anion having 1 to 10 carbon atoms or ligand represented by the following formula (3):

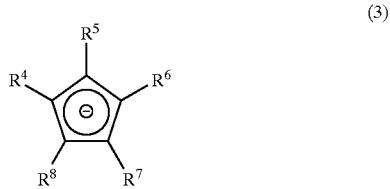

(3)

wherein $R^4$, $R^5$, $R^6$, $R^7$ and $R^8$ are each independently a hydrogen atom, hydrocarbon group having 1 to 10 carbon atoms or trimethylsilyl group, with the proviso that when at least two out of $R^4$, $R^5$, $R^6$, $R^7$ and $R^8$ are hydrocarbon groups having 1 to 10 carbon atoms, they may be bonded together to form a 4- to 8-membered ring, Y is a ligand represented by the following formula (4):

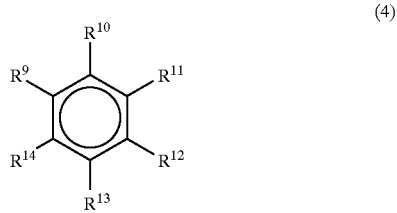

(4)

wherein $R^9$, $R^{10}$, $R^{11}$, $R^{12}$, $R^{13}$ and $R^{14}$ are each independently a hydrogen atom or hydrocarbon group having 1 to 10 carbon atoms, n is an integer of 1 to 3, m is an integer of 0 to 2, l is 0 or 1, and (n+m) is 3.

According to the present invention, secondly, the above object of the present invention is attained by a method of forming a ruthenium film from the above chemical vapor deposition material by chemical vapor deposition.

DETAILED DESCRIPTION OF THE PREFERRED EMBODIMENTS

Detailed description of the present invention are followed hereinafter.

The chemical vapor deposition material of the present invention is represented by the above formula (1).

In the above formula (1), L is represented by the above formula (2).

In the above formula (2), $R^1$, $R^2$ and $R^3$ are each independently a hydrogen atom, fluorine atom, trifluoromethyl group or hydrocarbon group having 1 to 10 carbon atoms. The hydrocarbon group having 1 to 10 carbon atoms is preferably a hydrocarbon group having 1 to 6 carbon atoms, as exemplified by methyl group, ethyl group, n-propyl group, isopropyl group, n-butyl group, isobutyl group, t-butyl group, neopentyl group, n-hexyl group and cyclohexyl group. As for preferred examples of $R^1$, $R^2$ and $R^1$, $R^3$ are each preferably an isopropyl group, t-butyl group, neopentyl group or cyclohexyl group, and $R^2$ is preferably a hydrogen atom, methyl group, ethyl group or t-butyl group.

In the above formula (1), X is a hydrogen anion, halogen anion, monovalent hydrocarbon anion having 1 to 10 carbon atoms or ligand represented by the above formula (3).

In the above formula (3), $R^4$, $R^5$, $R^6$, $R^7$ and $R^8$ are each independently a hydrogen atom, hydrocarbon group having 1 to 10 carbon atoms or trimethylsilyl group. When at least two out of $R^4$, $R^5$, $R^6$, $R^7$ and $R^8$ are hydrocarbon groups having 1 to 10 carbon atoms, they may be bonded together to form a 4- to 8-membered ring. Examples of the hydrocarbon group having 1 to 10 carbon atoms include methyl group and ethyl group. As an example where they are bonded together to form a ring, two adjacent carbon atoms out of carbon atoms forming a 5-membered ring of the above formula (3) are bonded to carbon atoms at the first-position and fourth-position of a group —$CH_2CH_2CH_2CH_2$— to form a six-membered ring.

In the above formula (4), $R^9$, $R^{10}$, $R^{11}$, $R^{12}$, $R^{13}$ and $R^{14}$ are each independently a hydrogen atom or hydrocarbon group having 1 to 10 carbon atoms. The hydrocarbon group having 1 to 10 carbon atoms is preferably an alkyl group having 1 to 4 carbon atoms, as exemplified by methyl group and ethyl group.

X in the above formula (1) is preferably a hydrogen anion, chlorine anion, methyl anion, ethyl anion, $\eta^5$-cyclopentadienyl group, $\eta^5$-tetramethylcyclopentadienyl group, $\eta^5$-trimethylsilylcyclopentadienyl group, $\eta^5$-indenyl group, $\eta^6$-benzene or $\eta^6$-toluene, more preferably a hydrogen anion, methyl anion or $\eta^5$-cyclopentadienyl group.

In the above formula (1), n is an integer of 1 to 3, m is an integer of 0 to 2, l is 0 or 1, and (n+m) is 3.

Illustrative examples of the chemical vapor deposition material represented by the above formula (1) include tris($\eta^3$-N,N'-diisopropylacetamidinate)ruthenium, bis($\eta^3$-N,N'-diisopropylacetamidinate)ruthenium chloride, ($\eta^3$-N,N'-diisopropylacetamidinate)ruthenium dichloride, tris($\eta^3$-N,N'-di-t-butylacetamidinate)ruthenium, bis($\eta^3$-N,N'-di-t-butylacetamidinate)ruthenium chloride, ($\eta^3$-N,N'-di-t-butylacetamidinate)ruthenium dichloride, tris($\eta^3$-N,N'-dicyclohexylacetamidinate)ruthenium, bis($\eta^3$-N,N'-dicyclohexylacetamidinate)ruthenium chloride, ($\eta^3$-N,N'-dicyclohexylacetamidinate)ruthenium dichloride, tris($\eta^3$-N-t-butyl-N'-ethylacetamidinate)ruthenium, bis($\eta^3$-N-t-butyl-N'-ethylacetamidinate)ruthenium chloride, ($\eta^3$-N-t-butyl-N'-ethylacetamidinate)ruthenium dichloride, bis($\eta^3$-N,N'-diisopropylacetamidinate)ruthenium hydride, ($\eta^3$-N,N'-diisopropylacetamidinate)ruthenium dihydride, bis($\eta^3$-N,N'-di-t-butylacetamidinate)ruthenium hydride, ($\eta^3$-N,N'-di-t-butylacetamidinate)ruthenium dihydride, bis($\eta^3$-N,N'-dicyclohexylacetamidinate)ruthenium hydride, ($\eta^3$-N,N'-dicyclohexylacetamidinate)ruthenium dihydride, bis(3-N-t-butyl-N'-ethylacetamidinate)ruthenium hydride, ($\eta^3$-N-t-butyl-N'-ethylacetamidinate)ruthenium dihydride, bis($\eta^3$-N,N'-diisopropylacetamidinate)methyl ruthenium, ($\eta^3$-N,N'-diisopropylacetamidinate)dimethyl ruthenium, bis($\eta^3$—N,N'-di-t-butylacetamidinate)methyl ruthenium, ($\eta^3$-N,N'-di-t-butylacetamidinate)dimethyl ruthenium, bis($\eta^3$-N,N'-dicyclohexylacetamidinate)methyl ruthenium, ($\eta^3$-N,N'-dicyclohexylacetamidinate)dimethyl ruthenium, bis($\eta^3$-N-t-butyl-N'-ethylacetamidinate)methyl ruthenium, ($\eta^3$-N-t-butyl-N'-ethylacetamidinate)dimethyl ruthenium, bis($\eta^3$-N,N'-diisopropylacetamidinate)($\eta^5$-cyclopentadienyl) ruthenium, ($\eta^3$-N,N'-diisopropylacetamidinate)di($\eta^5$-cyclopentadienyl) ruthenium, bis($\eta^3$-N,N'-di-t-butylacetamidinate)($\eta^5$-cyclopentadienyl) ruthenium, ($\eta^3$—N,N'-di-t-butylacetamidinate)di($\eta^5$-cyclopentadienyl) ruthenium, bis($\eta^3$-N,N'-dicyclohexylacetamidinate)($\eta^5$-cyclopentadienyl)ruthenium, ($\eta^3$-N,N'-dicyclohexylacetamidinate)di($\eta^5$-cyclopentadienyl)ruthenium, bis($\eta^3$-N-t-butyl-N'-ethylacetamidinate) ($\eta^5$-cyclopentadienyl)ruthenium and ($\eta^3$-N-t-butyl-N'-ethylacetamidinate)di($\eta^5$-cyclopentadienyl)ruthenium.

Out of these, preferred are tris($\eta^3$-N,N'-diisopropylacetamidinate)ruthenium, bis($\eta^3$-N,N'-diisopropylacetamidinate)ruthenium chloride, ($\eta^3$-N,N'-diisopropylacetamidinate)ruthenium dichloride, tris($\eta^3$-N,N'-di-t-butylacetamidinate)ruthenium, bis($\eta^3$-N,N'-di-t-butylacetamidinate)ruthenium chloride, ($\eta^3$-N,N'-di-t-butylacetamidinate)ruthenium dichloride, tris($\eta^3$-N,N'-dicyclohexylacetamidinate)ruthenium, bis($\eta^3$-N,N'-dicyclohexylacetamidinate)ruthenium chloride and ($\eta^3$-N,N'-dicyclohexylacetamidinate)ruthenium dichloride.

These compounds as a chemical vapor deposition material may be used alone or in combination of two or more. Preferably, they are used alone.

The above ruthenium compound can be synthesized by the general method of synthesizing a metal complex in accordance with the method disclosed in Inorg. Chem., 44(6), pp. 1728–1735 (2005). For example, it can be synthesized by reacting ruthenium halide with an alkali metal salt of a desired ligand in the presence of a suitable solvent. To synthesize a ruthenium compound having different ligands, ruthenium halide is reacted with a predetermined amount of an alkali metal salt of one ligand and then with a predetermined amount of an alkali metal salt of another ligand.

The halogen atom contained in the above ruthenium halide is preferably a chlorine atom or bromine atom, and the alkali metal contained in the alkali metal salt of the ligand is preferably lithium, sodium or potassium.

The above chemical vapor deposition material is used in the chemical vapor deposition of the present invention.

The chemical vapor deposition of the present invention may be a process known per se except that the above chemical vapor deposition material is used. For instance, it can be carried out as follows.

(1) The chemical vapor deposition material of the present invention is vaporized, and then (2) the resulting vapor is thermally decomposed by heating to deposit ruthenium on a substrate. Even when the above step (1) is accompanied by the decomposition of the chemical vapor deposition material of the present invention, the effect of the present invention is not lessened.

The substrate which can be used herein is made of a suitable material such as glass, silicon semiconductor, quartz, metal, metal oxide or synthetic resin. It is preferably a material which can stand the temperature of the step of thermally decomposing the ruthenium compound.

In the above step (1), the temperature for vaporizing the ruthenium compound is preferably 50 to 350° C., more preferably 80 to 300° C.

In the above step (2), the temperature for thermally decomposing the ruthenium compound is preferably 80 to 500° C., more preferably 100 to 400° C., most preferably 120 to 350° C.

The chemical vapor deposition of the present invention may be carried out in the presence or absence of an inert gas or the presence or absence of a reduction gas. Alternatively, it may be carried out in the presence of both the inert gas and the reduction gas. Examples of the inert gas include nitrogen, argon and helium. Examples of the reduction gas include hydrogen and ammonia. When the chemical vapor deposition material represented by the above formula (1) contains elemental halogen, the chemical vapor deposition is preferably carried out in the presence of a reduction gas.

The chemical vapor deposition of the present invention can be carried out in the coexistence of an oxidizing gas. Examples of the oxidizing gas include oxygen and nitrous oxide. When the oxidizing gas is coexistent, the amount of the oxidizing gas in the atmosphere is preferably 1 to 70 mol %, more preferably 3 to 40 mol %.

The chemical vapor deposition of the present invention can be carried out under increased pressure, normal pressure or reduced pressure. It is preferably carried out under normal pressure or reduced pressure, more preferably under a pressure of 15,000 Pa or less.

The ruthenium film thus obtained has high purity and high electric conductivity as obvious from Examples which are given hereinafter. A super thin ruthenium film having a thickness of 10 nm or less can be formed from the chemical vapor deposition material of the present invention and can be advantageously used as a barrier film for wiring electrodes and a capacitor electrode.

As described above, according to the present invention, there are provided a chemical vapor deposition material which can provide a high-quality ruthenium film even when it is very thin and a simple method of forming a ruthenium film from the chemical vapor deposition material.

EXAMPLES

The following examples are provided to further illustrate the present invention.

Synthetic Example 1

5.7 g of N,N'-diisopropylacetamidine was weighed and placed in a 200 ml flask whose inside had been substituted by nitrogen and left at 50° C. under reduced pressure for 60 minutes. After the inside temperature of the flask was returned to room temperature, the flask was filled with dry nitrogen. 50 ml of well dried diethyl ether was added to the flask in a nitrogen atmosphere and stirred to dissolve the above N,N'-diisopropylacetamidine. This solution was cooled to −60° C., and 22 ml of a diethyl ether solution of butyl lithium (concentration of 2.0 mol/l) was added dropwise under agitation over 30 minutes and further stirred for another 3 hours. Agitation was stopped, the inside temperature of the flask was returned to room temperature over 2 hours, and the supernatant was collected with a syringe to obtain a diethyl ether solution of a lithium salt of N,N'-diisopropylacetamidine.

Meanwhile, 2.1 g of anhydrous ruthenium trichloride was weighed and placed in a 200 ml flask whose inside had been substituted by nitrogen and left at 50° C. under reduced pressure for 60 minutes. After the inside temperature of the flask was returned to room temperature, the flask was filled with dry nitrogen. 50 ml of well dried diethyl ether and 50 ml of well dried tetrahydrofuran were added to the flask in a nitrogen atmosphere to dissolve the above anhydrous ruthenium trichloride. This solution was cooled to −60° C., and the above prepared diethyl ether solution of a lithium salt of N,N'-diisopropylacetamidine was added dropwise under agitation over 60 minutes and further stirred at the same temperature for another 5 hours. Agitation was stopped, the inside temperature of the flask was returned to room temperature over 2 hours, and the solution was left for another 1 hour. After the formed precipitate was removed by decantation, part of the solvent was removed under reduced pressure, and the resulting solution was concentrated. The thus obtained viscous solution was subjected to column chromatography by using a mixed solvent of diethyl ether and tetrahydrofuran (mixing ratio of 1/1 (volume ratio)) and a neutral alumina column to collect a red brown portion. After concentration under reduced pressure, the solvent was removed by heating at 40° C. and 133 Pa for 2 hours to obtain 0.9 g of tris ($\eta^3$-N,N'-diisopropylacetamidinate)ruthenium as a red purple solid. The yield rate was 17%.

When the elemental analysis of the obtained solid was carried out, it contained 55.7% of carbon, 8.21% of hydrogen and 17.2% of nitrogen. As for the theoretical values of tris ($\eta^3$-N,N'-diisopropylacetamidinate)ruthenium, it contains 54.9% of carbon, 9.80% of hydrogen and 16.0% of nitrogen.

Synthetic Example 2

2.1 g of N,N'-diisopropylacetamidine was weighed and placed in a 100 ml flask whose inside had been substituted by nitrogen and left at 50° C. under reduced pressure for 60 minutes. After the inside temperature of the flask was returned to room temperature, the flask was filled with dry nitrogen. 20 ml of well dried diethyl ether was added to the flask in a nitrogen atmosphere and stirred to dissolve the above N,N'-diisopropylacetamidine. This solution was cooled to −60° C., and 9 ml of a diethyl ether solution of butyl lithium (concentration of 2.0 mol/l) was added dropwise under agitation over 30 minutes and further stirred for another 3 hours. Agitation was stopped, the inside temperature of the flask was returned to room temperature over 2 hours, and the supernatant was collected with a syringe to obtain a diethyl ether solution of a lithium salt of N,N'-diisopropylacetamidine.

Meanwhile, 2.1 g of anhydrous ruthenium trichloride was weighed and placed in a 200 ml flask whose inside had been substituted by nitrogen and left at 50° C. under reduced pressure for 60 minutes. After the inside temperature of the flask was returned to room temperature, the flask was filled with dry nitrogen. 50 ml of well dried diethyl ether and 50 ml of well dried tetrahydrofuran were added to the flask to dissolve the above anhydrous ruthenium trichloride. This solution was cooled to −60° C., and the above prepared diethyl ether solution of a lithium salt of N,N'-diisopropylacetamidine was added dropwise under agitation over 60 minutes and further stirred for another 5 hours. Agitation was stopped, the inside temperature of the flask was returned to room temperature over 2 hours, and the solution was left for another 1 hour. After the formed precipitate was removed by decantation, part of the solvent was removed under reduced pressure, and the resulting solution was concentrated. The thus obtained viscous solution was subjected to column chromatography by using a mixed solvent of diethyl ether and tetrahydrofuran (mixing ratio of 1/1 (volume ratio)) and a neutral alumina column to collect a red brown portion. After concentration under reduced pressure, the solvent was removed by heating at 40° C. and 133 Pa for 2 hours to obtain 1.3 g of ($\eta^3$-N,N'-diisopropylacetamidinate)ruthenium dichloride as a dark brown solid. The yield rate was 41%.

When the elemental analysis of the obtained solid was carried out, it contained 32.4% of carbon, 5.08% of hydrogen and 9.11% of nitrogen. As for the theoretical values of ($\eta^3$-N,N'-diisopropylacetamidinate)ruthenium dichloride, it contains 30.7% of carbon, 5.47% of hydrogen and 8.94% of nitrogen.

Synthetic Example 3

6.8 g of N,N'-di-t-butylacetamidine was weighed and placed in a 200 ml flask whose inside had been substituted by nitrogen and left at 50° C. under reduced pressure for 60 minutes. After the inside temperature of the flask was returned to room temperature, the flask was filled with dry nitrogen. 50 ml of well dried diethyl ether was added to the flask in a nitrogen atmosphere and stirred to dissolve the above N,N'-di-t-butylacetamidine. This solution was cooled to −60° C., 22 ml of a diethyl ether solution of butyl lithium (concentration of 2.0 mol/l) was added dropwise under agitation over 30 minutes and further stirred for another 3 hours. Agitation was stopped, the inside temperature of the flask was returned to room temperature over 2 hours, and the supernatant was collected with a syringe to obtain a diethyl ether solution of a lithium salt of N,N'-di-t-butylacetamidine.

Meanwhile, 2.1 g of anhydrous ruthenium trichloride was weighed and placed in a 200 ml flask whose inside had been substituted by nitrogen and left at 50° C. under reduced pressure for 60 minutes. After the inside temperature of the flask was returned to room temperature, the flask was filled with dry nitrogen. 50 ml of well dried diethyl ether and 50 ml of well dried tetrahydrofuran were added to the flask to dissolve the above anhydrous ruthenium trichloride. This solution was cooled to −60° C., and the above prepared diethyl ether solution of a lithium salt of N,N'-di-t-butylacetamidine was added dropwise under agitation over 60 minutes and further stirred for another 5 hours. Agitation was stopped, the inside temperature of the flask was returned to room temperature over 2 hours, and the solution was left for another 1 hour. After the formed precipitate was removed by decantation, part of the solvent was removed under reduced pressure, and the resulting solution was concentrated. The thus obtained viscous solution was subjected to column chromatography by using a mixed solvent of diethyl ether and tetrahydrofuran (mixing ratio of 1/1 (volume ratio)) and a neutral alumina column to collect a red brown portion. After concentration under reduced pressure, the solvent was removed by heating at 40° C. and 133 Pa for 2 hours to obtain 1.2 g of tris($\eta^3$-N,N'-di-t-butylacetamidinate)ruthenium as a red purple solid. The yield rate was 19%.

When the elemental analysis of the obtained solid was carried out, it contained 60.9% of carbon, 9.94% of hydrogen and 13.0% of nitrogen. As for the theoretical values of tris($\eta^3$-N,N'-di-t-butylacetamidinate)ruthenium, it contains 59.2% of carbon, 10.4% of hydrogen and 13.8% of nitrogen.

In the following examples, the resistivity was measured with the RT-80/RG-80 probe resistivity measuring instrument of Napson Co., Ltd. The film thickness and film density were measured with the X'Pert MRD grazing incidence X-ray analyzer of Philips Co., Ltd. The ESCA spectrum was measured with the JPS80 of JEOL Ltd. The adhesion was evaluated in accordance with a crosscut adhesion tape method specified in JIS K-5400.

Example 1

0.01 g of tris($\eta^3$-N,N'-diisopropylacetamidinate)ruthenium obtained in Synthetic Example 1 was weighed and placed in a quartz boat type vessel in an argon gas, and the vessel was set in a quartz reactor. A quartz substrate was placed at a position near a gas stream in the reactor, and a nitrogen gas was passed into the reactor at room temperature at a flow rate of 250 ml/min for 30 minutes. Thereafter, a nitrogen gas was passed into the reactor at a flow rate of 100 ml/min, the inside pressure of the system was set to 1,333 Pa, and the reactor was heated at 180° C. for 30 minutes. Mist was generated from the boat type vessel, and a deposit on the quartz substrate installed nearby was seen. After the end of the generation of the mist, depressurization was stopped, a nitrogen gas was passed at 101.3 kPa at a flow rate of 200 ml/min, and the inside temperature of the reactor was raised to 350° C. and maintained at that temperature for 1 hour. Then, a film having a metallic gloss was obtained on the substrate. The thickness of this film was 100 Å.

When the ESCA spectrum of this film was measured, peaks attributed to the $Ru_{3d}$ orbit were observed at 280 eV and 284 eV and no peak derived from another element was observed at all, which means that the film was made of metal ruthenium. When the resistivity of this ruthenium film was measured by the 4-terminal method, it was 38 $\mu\Omega$cm. The density of this film was 12.0 g/cm$^3$. When the adhesion of this ruthenium film to the substrate was evaluated by a crosscut adhesion tape method, no separation between the substrate and the ruthenium film was seen at all.

Example 2

0.01 g of ($\eta^3$-N,N'-diisopropylacetamidinate)ruthenium dichloride obtained in Synthetic Example 2 was weighed and placed in a quartz boat type vessel in an argon gas, and the vessel was set in a quartz reactor. A quartz substrate was placed at a position near a gas stream in the reactor, and a nitrogen gas was passed into the reactor at room temperature at a flow rate of 250 ml/min for 30 minutes. Thereafter, a mixed gas of hydrogen and nitrogen (hydrogen content of 3 vol %) was passed into the reactor at a flow rate of 30 ml/min, the inside pressure of the system was set to 80 Pa, and the reactor was heated at 170° C. for 40 minutes. Mist was generated from the boat type vessel, and a deposit on the quartz substrate installed nearby was seen. After the end of the generation of the mist, depressurization was stopped, a mixed gas of hydrogen and nitrogen (hydrogen content of 3%) was passed at 101.3 kPa at a flow rate of 500 ml/min, and the inside temperature of the reactor was raised to 350° C. and maintained at that temperature for 1 hour. Then, a film having a metallic gloss was obtained on the substrate. The thickness of this film was 95 Å.

When the ESCA spectrum of this film was measured, peaks attributed to the $Ru_{3d}$ orbit were observed at 280 eV and 284 eV and no peak derived from another element was observed at all, which means that the film was made of metal ruthenium. When the resistivity of this ruthenium film was measured by the 4-terminal method, it was 41 $\mu\Omega$cm. The density of this film was 11.6 g/cm$^3$. When the adhesion of this ruthenium film to the substrate was evaluated by the crosscut adhesion tape method, no separation between the substrate and the ruthenium film was seen at all.

Example 3

0.01 g of tris($\eta^3$-N,N'-di-t-butylacetamidinate)ruthenium obtained in Synthetic Example 3 was weighed and placed in a quartz boat type vessel in an argon gas, and the vessel was set in a quartz reactor. A quartz substrate was placed at a position near a gas stream in the reactor, and a nitrogen gas was passed into the reactor at room temperature at a flow rate of 250 ml/min for 30 minutes. Thereafter, a nitrogen gas was passed into the reactor at a flow rate of 100 ml/min, the inside pressure of the system was set to 1,333 Pa, and the reactor was heated at 170° C. for 30 minutes. Mist was generated from the boat type vessel, and a deposit on the quartz substrate installed nearby was seen. After the end of the generation of the mist, depressurization was stopped, a nitrogen gas was passed at 101.3 kPa at a flow rate of 200 ml/min, and the inside temperature of the reactor was raised to 350° C. and maintained at that temperature for 1 hour. Then, a film having a metallic gloss was obtained on the substrate. The thickness of this film was 98 Å.

When the ESCA spectrum of this film was measured, peaks attributed to the $Ru_{3d}$ orbit were observed at 280 eV and 284 eV and no peak derived from another element was observed at all, which means that the film was made of metal ruthenium. When the resistivity of this ruthenium film was measured by the 4-terminal method, it was 40 $\mu\Omega$cm. The density of this film was 12.1 g/cm$^3$. When the adhesion of this ruthenium film to the substrate was evaluated by the crosscut adhesion tape method, no separation between the substrate and the ruthenium film was seen at all.

Example 4

The procedure of Example 1 was repeated except that the amount of tris($\eta^3$-N,N'-diisopropylacetamidinate)ruthenium was changed to 0.005 g to obtain a 55 Å-thick film having a metallic gloss. When the ESCA spectrum of this film was measured, only peaks attributed to the $Ru_{3d}$ orbit were observed. The resistivity of this ruthenium film measured by the 4-terminal method was 48 $\mu\Omega$cm and the density of this film was 12.0 g/cm$^3$. When the adhesion of this ruthenium film to the substrate was evaluated by the crosscut adhesion tape method, no separation between the substrate and the ruthenium film was seen at all.

Comparative Example 1

The procedure of Example 1 was repeated except that 0.01 g of commercially available bisethylcyclopentadienyl ruthenium was used in place of tris($\eta^3$-N,N'-diisopropylacetamidinate)ruthenium and the heating temperature of the reactor was changed to 300° C. to obtain a 220 Å-thick film having a metallic gloss. When the ESCA spectrum of this film was measured, only peaks attributed to the $Ru_{3d}$ orbit were observed, which means that this film was made of metal ruthenium. When the resistivity of this ruthenium film was measured by the 4-terminal method, it was 125 $\mu\Omega$cm. When the adhesion of this ruthenium film to the substrate was evaluated by the crosscut adhesion tape method, all the 100 squares were removed. The density of this film was 11.2 g/cm$^3$.

Comparative Example 2

The procedure of Comparative Example 1 was repeated except that the amount of bisethylcyclopentadienyl ruthenium was changed to 0.005 g to obtain a film having a metallic gloss. The thickness of the obtained film was not uniform and varied from 60 to 190 Å. When the ESCA spectrum of this film was measured, only peaks attributed to the $Ru_{3d}$ orbit were observed. When the resistivity of this ruthenium film was measured by the 4-terminal method, it was 167 $\mu\Omega$cm, and the density of this film was 11.2 g/cm$^3$. When the adhesion of this ruthenium film to the substrate was evaluated by the crosscut adhesion tape method, all the 100 squares were removed.

What is claimed is:

1. A chemical vapor deposition material represented by the following formula (1):

$$Ru^{3+}+L_nX_mY_l \quad (1)$$

wherein L is a ligand represented by the following formula (2):

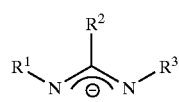
(2)

wherein $R^1$, $R^2$ and $R^3$ are each independently a hydrogen atom, fluorine atom, trifluoromethyl group or hydrocarbon group having 1 to 10 carbon atoms, X is a hydrogen anion, halogen anion, monovalent hydrocarbon anion having 1 to 10 carbon atoms or ligand represented by the following formula (3):

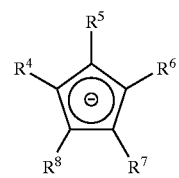
(3)

wherein $R^4$, $R^5$, $R^6$, $R^7$ and $R^8$ are each independently a hydrogen atom, hydrocarbon group having 1 to 10 carbon atoms or trimethylsilyl group, with the proviso that when at least two out of $R^4$, $R^5$, $R^6$, $R^7$ and $R^8$ are hydrocarbon groups having 1 to 10 carbon atoms, they may be bonded together to form a 4- to 8-membered ring, Y is a ligand represented by the following formula (4):

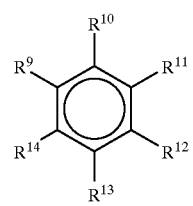
(4)

where in $R^9$, $R^{10}$, $R^{11}$, $R^{12}$, $R^{13}$ and $R^{14}$ are each independently a hydrogen atom or hydrocarbon group having 1 to 10 carbon atoms, n is an integer of 1 to 3, m is an integer of 0 to 2, l is 0 or 1, and (n+m) is 3.

2. A method of forming a ruthenium film, which comprises subjecting the chemical vapor deposition material of claim 1 to chemical vapor deposition.

* * * * *